United States Patent [19]
Ken

[11] Patent Number: 6,113,629
[45] Date of Patent: Sep. 5, 2000

[54] HYDROGEL FOR THE THERAPEUTIC TREATMENT OF ANEURYSMS

[75] Inventor: Christopher G. M. Ken, San Mateo, Calif.

[73] Assignee: Micrus Corporation, Mountain View, Calif.

[21] Appl. No.: 09/071,250

[22] Filed: May 1, 1998

[51] Int. Cl.[7] .................................................. A61F 2/06
[52] U.S. Cl. ............................ 623/1.1; 604/49; 604/96; 606/213
[58] Field of Search ....................... 623/1, 11, 12; 604/96, 100, 49, 53; 606/108, 213; 424/426; 514/21

[56] References Cited

U.S. PATENT DOCUMENTS

| | | |
|---|---|---|
| 2,726,982 | 12/1955 | Ochs et al. . |
| 4,565,784 | 1/1986 | Franzblau et al. . |
| 4,795,741 | 1/1989 | Leshchiner et al. ....................... 514/21 |
| 4,878,907 | 11/1989 | Okada et al. . |
| 5,213,580 | 5/1993 | Slepian et al. . |
| 5,213,720 | 5/1993 | Civerchia . |
| 5,258,042 | 11/1993 | Mehta . |
| 5,328,471 | 7/1994 | Slepian . |
| 5,410,016 | 4/1995 | Hubbell et al. . |
| 5,514,379 | 5/1996 | Weissleder et al. ..................... 424/426 |
| 5,522,888 | 6/1996 | Civerchia . |
| 5,575,815 | 11/1996 | Slepian et al. . |
| 5,580,568 | 12/1996 | Greff et al. . |
| 5,604,200 | 2/1997 | Taylor-McCord . |
| 5,624,685 | 4/1997 | Takahashi et al. ....................... 424/488 |
| 5,626,863 | 5/1997 | Hubbell et al. . |
| 5,634,936 | 6/1997 | Linden et al. . |
| 5,634,946 | 6/1997 | Slepian . |
| 5,662,609 | 9/1997 | Slepian . |
| 5,665,063 | 9/1997 | Roth et al. . |
| 5,667,767 | 9/1997 | Greff et al. ........................... 424/9.411 |
| 5,674,287 | 10/1997 | Slepian et al. . |

FOREIGN PATENT DOCUMENTS

| | | |
|---|---|---|
| 0 547 530 A1 | 6/1993 | European Pat. Off. . |
| WO 98/55174 | 11/1997 | WIPO . |
| WO 97/45131 | 12/1997 | WIPO . |
| WO 97/40849 | 12/1998 | WIPO . |
| WO 99/29260 | 6/1999 | WIPO . |

OTHER PUBLICATIONS

Copy of the International Search Report Relating to PCT/US99/09492 Dated Aug. 17, 1999.
Patent Abstracts of Japan Publication No. 05017369, Publication Date Jan. 26, 1993.

Primary Examiner—Mickey Yu
Assistant Examiner—Choon P. Koh
Attorney, Agent, or Firm—Fulwider Patton Lee & Utecht, LLP

[57] ABSTRACT

The hydrogel for the treatment of aneurysms acts as a carrier for both a radiopaque agent allowing the hydrogel to be visualized under fluoroscopy and a therapeutic agent such as one or more human growth factors. The hydrogel is delivered through a catheter into the aneurysm, where the hydrogel becomes more viscous upon reaching body temperature, or upon exposure to bodily fluids, to block blood flow into the aneurysm. In addition to stopping blood flow into the aneurysm, the delivery of human growth factors to the aneurysm site promotes the growth of a cellular layer across the neck of the aneurysm. The hydrogel may be of a type that dissolves over time or one which remains as a permanent occlusive agent within the aneurysm.

10 Claims, No Drawings

HYDROGEL FOR THE THERAPEUTIC TREATMENT OF ANEURYSMS

BACKGROUND OF THE INVENTION

1. Field of the Invention

This invention relates generally to treatment of vascular aneurysms, and more particularly concerns the use of hydrogels for use in occluding aneurysms and in controlled drug delivery for treatment of aneurysms.

2. Description of Related Art

Aneurysms have been traditionally treated with externally placed clips, or internally by detachable vasoocclusive balloons or an embolus generating vasoocclusive device such as one or more vasoocclusive coils. The delivery of such vasoocclusive devices can be accomplished by a variety of means, including via a catheter in which the device is pushed through the catheter by a pusher to deploy the device. The vasoocclusive devices can be produced in such a way that they will pass through the lumen of a catheter in a linear shape and take on a complex shape as originally formed after being deployed into the area of interest, such as an aneurysm. In current techniques, the vasoocclusive devices take the form of spiral wound wires that can take more complex three dimensional shapes as they are inserted into the area to be treated. By using materials that are highly flexible, or even super-elastic and relatively small in diameter, the wires can be installed in a micro-catheter in a relatively linear configuration and assume a more complex shape as it is forced from the distal end of the catheter.

Adhesives that have been introduced to help heal aneurysms include cyanoacrylates, gelatin/resorcinol/formol, mussel adhesive protein and autologous fibrinogen adhesive. Fibrin gels have also been used as sealants and adhesives in surgery, and hydrogels have been used as sealants for bleeding organs, and to create tissue supports for the treatment of vascular disease by the formation of shaped articles to serve a mechanical function. Catheters have commonly been used to introduce such therapeutic agents locally at diseased occluded regions of the vasculature to promote vessel healing. Typically a polymeric paving and sealing material in the form of a monomer solution, prepolymer solution, or as a preformed or partially preformed polymeric product, is introduced into the lumen of the blood vessel and positioned at the point of a stenosis. The polymeric material typically can incorporate additional therapeutic agents such as drugs, drug producing cells, cell regeneration factors, and progenitor cells either of the same type as the vascular tissue of the aneurysm, or histologically different to accelerate the healing process.

Hydrogels have also been used to form expanding, swelling stents, and as space-fillers for treatment of vascular aneurysms in a manner similar to other types of mechanical, embolus generating vasoocclusive devices. In one such procedure, an aneurysm is treated by inserting a stent formed of a hydrogel material into the vessel, and then hydrating and expanding the hydrogel material until the stent occludes the vascular wall, sealing it from the parent vessel. Biodegradable hydrogels have also been used as controlled-release carriers for biologically active materials such as hormones, enzymes, antibiotics, antineoplastic agents, and cell suspensions.

From the above, it can be seen that vasoocclusive devices and materials and their deployment systems provide valuable treatments for diseased vascular regions. However, there remain important limitations in the technology presently available, since treating an aneurysm with adhesive or occluding the aneurysm with a stent may not be completely effective in healing the vascular damage. Furthermore, when an embolus generating vasoocclusive device or space-filling device such as a vasoocclusive coil is used to treat an aneurysm, the ability to treat the aneurysm depends upon whether the embolus generating vasoocclusive device can migrate out of the aneurysm through the neck of the aneurysm. It would therefore be desirable to provide a method for sealing off the neck of an aneurysm or all of the aneurysm, either in addition to or as an alternative to the introduction of a vasoocclusive device in the aneurysm, in order to prevent the danger of migration of an embolus generating device out of the aneurysm, to avoid the danger to a patient from the bursting of the aneurysm, and to promote healing of the diseased vasculature, in a manner that can be visualized under fluoroscopy. The present invention meets these and other needs.

SUMMARY OF THE INVENTION

The present invention solves these and other problems by providing, in its broadest aspect, an improved method for treating an aneurysm by delivering a hydrogel carrying growth factors to promote cellular growth across the neck of the aneurysm, to eliminate and heal the aneurysm with the body's own cellular growth. In addition to delivering the growth factor, the hydrogel acts as an embolic agent blocking the flow of blood into the aneurysm and eliminating the chance for hemorrhage, and can be used either separately, or in combination with other occlusive, embolus generating devices in treatment of aneurysms.

Briefly, and in general terms, a presently preferred embodiment of the present invention provides for a method for the treatment of aneurysms nonmechanically, through the delivery of human growth factors and/or gene therapy to the site of an aneurysm. The invention utilizes a hydrogel that acts as a carrier for both a radiopaque agent allowing the hydrogel to be visualized under fluoroscopy and a therapeutic agent such as one or more human growth factors. The hydrogel is delivered through a catheter into the aneurysm, where, in one currently preferred embodiment, the hydrogel becomes more viscous upon reaching body temperature, or upon exposure to bodily fluids. In our presently preferred embodiment, the hydrogel is constituted so as to remain a liquid at temperatures below about 37° C., to thereby facilitate the placement and retention of the gel and gel contained agents within the aneurysm. The hydrogel preferably then solidifies to block blood flow into the aneurysm. In addition to stopping blood flow into the aneurysm, the delivery of human growth factors to the aneurysm site promotes the growth of a cellular layer across the neck of the aneurysm. The hydrogel may be of a type that dissolves over time or one which remains as a permanent occlusive agent within the aneurysm.

These and other aspects and advantages of the invention will become apparent from the following detailed description.

DETAILED DESCRIPTION OF THE PREFERRED EMBODIMENTS

Treatment of an aneurysm by sealing it with adhesive, blocking it with a stent, or placement of a vasoocclusive device to occlude it may not be completely effective in healing the vascular damage. A vasoocclusive or space-filling device placed within an aneurysm can also migrate out of the aneurysm through the neck of the aneurysm.

The invention accordingly provides for a hydrogel that acts as a carrier for both a radiopaque agent allowing the hydrogel to be visualized under fluoroscopy and a therapeutic agent such as one or more human growth factors. As used in this application, the term "hydrogel" refers to a broad class of polymeric materials that have an affinity for water and typically swell in water, but which do not necessarily dissolve in water. In general, hydrogels are formed by polymerization and crosslinking of a hydrophilic monomer in an aqueous solution to cause the solution to gel. In a presently preferred embodiment, the hydrogel can be constituted to be liquid at a temperature below body temperature and to gel at body temperature so that the gel can be easily introduced into the aneurysm, but rapidly gels in the space to occlude at least a portion of the aneurysm.

The hydrogel of the present invention can be one or more hydrogels selected from organic gels and inorganic gels. Organic gels from which the hydrogel of the invention can be selected include, by way of example and not by way of limitation, gels formed from polysaccharides and mucopolysaccharides including, but not limited to hyaluronic acid, dextran, heparin sulfate, chondroitin sulfate, heparin, agar, starch, and alginate; polyaminoacids; proteins that support cell growth and healing, including but not limited to fibronectin, gelatin, collagen, fibrin, pectins, albumin, ovalbumin, and polyamino acids; collagen-hydroxyethyl-methacrylate (HEMA); polyphosphazines; polyphosphoesters; polyethylene glycol; polyethylene oxide; polyvinyl alcohol; polyvinylpyrrolidone; polyethyloxazoline; polyethylene oxide-co-polypropyleneoxide block copolymers; PGA-PEG-PGA block copolymers; PGA-PEG diblock copolymers; acrylates, including but not limited to diacrylates, oligoacrylates, methacrylates, dimethacrylates and oligomethoacrylates; PEG-oligoglycolylacrylates, such as described in U.S. Pat. No. 5,626,863, which is incorporated by reference herein; carboxy alkyl celluloses, including but not limited to carboxymethyl cellulose; partially oxidized cellulose; biodegradable polymers including but not limited to polymers and oligomers of glycolide, lactide, polylactic acid, polyesters of α-hydroxy acids, including lactic acid and glycolic acid, such as the poly(α-hydroxy) acids including polyglycolic acid, poly-DL-lactic, poly-L-lactic acid, and terpolymers of DL-lactide and glycolide; ε-caprolactone and ε-caprolactone copolymerized with polyesters; polylactones and polycaprolactones including poly(ε-caprolactone), poly(δ-valerolactone) and poly (gamma-butyrolactone); polyanhydrides; polyorthoesters; other hydroxy acids; polydioxanone; and other biologically degradable polymers that are non-toxic or are present as metabolites in the body; as well as non-degradable polymers such as styrene and acrolein.

Collagen-hydroxyethyl-methacrylate (EMA) hydrogel polymer is commonly formed from a gelled and crosslinked hydrophilic monomer solution to form a three dimensional polymeric meshwork anchoring macromolecules. Crosslinking of the hydrophilic monomer solution can be accomplished by free radical polymerization of hydrophilic monomers, such as hydroxyethyl-methacrylate (HEMA). Hydrogel polymers formed by free radical polymerization of monomer solutions require crosslinking to form the three dimensional network to gel the aqueous solution. HEMA monomer solutions typically can be crosslinked to gel by dimethacrylate, although other crosslinking agents, such as ethylene glycol dimethacrylate or methylmethacrylate, can also be used during polymerization to modify the hydrogel. A wide variety of other hydrophilic monomers may also be suitable for purposes of the invention.

Inorganic gels from which the hydrogel of the invention can be selected include, by way of example and not by way of limitation, silica, alumina, and ferric oxide. In addition, an adhesive can be introduced via a catheter to initially help seal the neck of an aneurysm, and can be selected from the group consisting of cyanoacrylates, gelatin/resorcinol/formol, mussel adhesive protein and autologous fibrinogen adhesive. It should thus be apparent that the hydrogel of the invention can be of a type that dissolves over time or one that remains as a permanent occlusive agent within the aneurysm.

The radiopaque material that is incorporated into the hydrogel of the invention is preferably fine particles of a selected radiopaque metal, such as gold, platinum, tantalum or the like. The therapeutic agent incorporated into the hydrogel of the invention is preferably one or more human growth modulating factors such as interleukins, transformation growth factor b, gene therapy agents, congeners of platelet derived growth factor, and monoclonal antibodies directed against growth factors, drugs, drug producing cells, cell regeneration factors, progenitor cells of the same type as those from the aneurysm, and progenitor cells that are histologically different from those of the aneurysm, to accelerate the healing process. The therapeutic agent can be administered in the form of fine particles mixed with the polymer so that it gels within the aneurysm to concentrate the effect of the therapeutic agent within the aneurysm.

According to the method of the invention, a catheter is typically positioned in a parent vessel of the aneurysm, and the hydrogel of the invention is delivered through the catheter into the aneurysm, where the hydrogel becomes more viscous upon reaching body temperature, or upon exposure to bodily fluids. During introduction of the hydrogel into the aneurysm, the hydrogel can be imaged by common fluoroscopic techniques to allow the physician to monitor the treatment of the aneurysm. Once introduced into the aneurysm, the hydrogel preferably further crosslinks to solidify to block blood flow into the aneurysm, and the one or more therapeutic agents carried by the hydrogel gradually diffuse and disperse from the hydrogel into the aneurysm, to promote the growth of a cellular layer across the neck of the aneurysm.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for treating an aneurysm, the aneurysm having a dome portion and a neck opening into a parent vessel, the method comprising the steps of:

introducing an embalus generating vasoocclusive device into the aneurysm; and delivering a hydrogel into the dome portion of the aneurysm and adjacent to the neck of the aneurysm, the hydrogel containing a radiopaque material and a therapeutic agent that is released from the hydrogel in the aneurysm to promote cellular growth across the neck of the aneurysm to close the neck of the aneurysm.

2. The method of claim 1, wherein said hydrogel is selected from the group consisting of organic gels and inorganic gels.

3. The method of claim 1, wherein said hydrogel is selected from the group consisting of biodegradable polymers and non-degradable polymers.

4. The method of claim 1, wherein said hydrogel is selected from the group consisting of gels formed from polysaccharides, mucopolysaccharides, polyaminoacids, proteins that support cell growth and healing, polyphosphazines, polyphosphoesters, polyethylene glycol, polyethylene oxide, polyvinyl alcohol, polyvinylpyrrolidone, polyethyloxazoline, polyethylene oxide-co-polypropyleneoxide block copolymers, PGA-PEG-PGA block copolymers, PGA-PEG diblock copolymers, acrylates, carboxy alkyl celluloses, partially oxidized cellulose, polymers and oligomers of glycolide and lactide, polylactic acid, polyesters of $\alpha$-hydroxy acids, polylactones, polycaprolactones, polyanhydrides, polyorthoesters, polydioxanone, styrene, acrolein and combinations thereof.

5. The method of claim 1, wherein said hydrogel is selected from the group consisting of gels formed from hyaluronic acid, dextran, heparin sulfate, chondroitin sulfate, heparin, agar, starch, alginate, fibronectin, gelatin, collagen, fibrin, pectins, albumin, ovalbumin, collagen-hydroxyethyl-methacrylate (HEMA); diacrylates, oligoacrylates, methacrylates, dimethacrylates, oligomethoacrylates, PEG-oligoglycolylacrylates, carboxymethyl cellulose, polyesters of lactic acid, polyesters of glycolic acid, poly($\alpha$-hydroxy) acids including polyglycolic acid, poly-DL-lactic, poly-L-lactic acid, and terpolymers of DL-lactide and glycolide, $\epsilon$-caprolactone, $\epsilon$-caprolactone copolymerized with polyesters, poly($\epsilon$-caprolactone), poly($\delta$-valerolactone), poly(gamma-butyrolactone), and combinations thereof.

6. The method of claim 1, wherein said hydrogel is selected from the group consisting of gels formed from silica, alumina, ferric oxide, and combinations thereof.

7. The method of claim 1, wherein said radiopaque material is selected from the group consisting of fine particles of gold, platinum, tantalum and combinations thereof.

8. The method of claim 1, wherein said therapeutic agent is selected from the group consisting of interleukins, transformation growth factor b, congeners of platelet derived growth factor, and monoclonal antibodies directed against growth factors, drugs, drug producing cells, cell regeneration factors, progenitor cells of the same type as those from the aneurysm, and progenitor cells that are histologically different from those of the aneurysm.

9. The method of claim 1, wherein said therapeutic agent is a growth factor.

10. The method of claim 1, wherein said hydrogel is constituted to be a liquid at a temperature below body temperature and gels at body temperature.

* * * * *

UNITED STATES PATENT AND TRADEMARK OFFICE
Certificate

Patent No. 6,113,629

Patented: September 5, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christopher G. M. Ken, San Mateo, CA; and J. Todd Derbin, Palo Alto, CA.

Signed and Sealed this Sixth Day of July 2004.

NICHOLAS D. LUCCHESI
*Supervisory Patent Examiner*
Art Unit 3764